US00PP10735P

United States Patent [19]

Wain

[11] Patent Number: Plant 10,735

[45] Date of Patent: Dec. 22, 1998

[54] CHRYSANTHEMUM PLANT NAMED 'MOVIE TIME'

[75] Inventor: Peter Wain, Portsmouth, United Kingdom

[73] Assignee: Cleangro, Ltd., West Sussex, England

[21] Appl. No.: 838,354

[22] Filed: Apr. 8, 1997

[51] Int. Cl.[6] ..... A01H 5/00

[52] U.S. Cl. ..... Plt./82.2

[58] Field of Search ..... Plt./74.1, 82.2

*Primary Examiner*—Howard J. Locker
*Attorney, Agent, or Firm*—Christie, Parker & Hale, LLP

[57] ABSTRACT

A new variety of Chrysanthemum plant having yellow ray florets with brighter yellow disc florets with maroon tips.

1 Drawing Sheet

BACKGROUND OF THE INVENTION

The present invention is directed to a new and distinct variety of Chrysanthemum botanically classified as *Dendranthema grandiflora*. The varietal denomination of the new Chrysanthemum is 'Movie Time.'

The female and male parents of the new variety are undistributed, unpatented seedlings identified as P24-14 and P19-26, respectively. The new variety has been asexually reproduced by vegetative cuttings in Ventura County, Calif. and the distinguishing characteristics are retained through successive generations of asexual reproduction.

SUMMARY OF THE INVENTION

'Movie Time' is a spray type, pot forcing Chrysanthemum plant variety producing flowers with yellow ray florets with brighter yellow disc florets with maroon tips, and capable of being grown commercially in a greenhouse.

BRIEF DESCRIPTION OF ILLUSTRATION

The accompanying photograph shows a typical specimen of the new variety with colors being as nearly true as possible with illustrations of this type.

DESCRIPTION OF THE PLANT

The following description of the new variety is of specimens grown in a greenhouse in Ventura County, Calif. in the month of October. 'Movie Time' has not been observed under all possible environmental conditions. The phenotype may vary significantly with variations in the environment such as temperature, light intensity, day length and cultural conditions. Color values provided in the description are from The Royal Horticultural Society Colour Charts (R.H.S.C.C.), unless otherwise indicated.

Plants of the new variety have been grown successfully under temperature conditions averaging about 65° F. at night and about 78° F. during the day with clear summer light. The plants respond well to use of growth retardant, such as one treatment of growth regulator B-9 at about 2500 ppm. To produce a commercial product the plants may be pinched once with the center bud removed. It has been observed that the shelf life of 'Movie Time' is about 24 days with the response time of about 8 weeks.

Plant

Habit: Upright.
Height: About 31 cm after treatment with growth regulator as described above.

Branching characteristics: Free branching at each node, also 1–2 underground branches per cutting.
Number of breaks from pinch: Average about 3 per stem.
Typical container size to be grown in: 4", 6", 8", 10".
Length of lateral branches:
*Average.*—About 20 cm. stem color: Near 146C.

Foliage

Leaf arrangement: Alternate.
Number of leaves per lateral Branch:
*Average number of leaves per lateral branch.*—About 10 fully mature leaves per 20 cm branch, abundant immature leaves; stem color near 146C.
(1) *Size.*—Length — Average about 8 cm. Width — Average about 4.2 cm.
(2) *Shape.*—Elliptic.
(3) *Attachment.*—Stalked.
(4) *Apex.*—Obtuse with serrate tip.
(5) *Base.*—Tapered.

| (6) | Color: | Mature | Young |
|---|---|---|---|
| | Top: | Near 137A | Near 137C |
| | Bottom: | Near 138B | Near 137D |

Margin: 5-lobed, slight serrations.
Aspect: Flat with some curving under or up.
Surface characteristics: Top—puberulent; Bottom—puberulent.
Venation: Palmately net, veins prominent in underside of leaf, color near 145C.
Petiole:
(1) *Length.*—About 1.8 cm.
(2) *Color.*—Near 145B.
(3) *Other Characteristics.*—Winged.
Stipule: 2 at every mature leaf, 3-lobed, average about 1.1 cm long and 1.6 cm wide.

Flower

Inflorescence form: Cymose cluster.
Flower form: Anemone.
Flower shape: Flat.
Flower color (general): Yellow ray florets with brighter yellow disc florets with maroon tips.
Bloom: Average about 30 blooms per pinched stem.
(1) *Diameter.*—Average about 5 cm.
(2) *Depth.*—Average about 1.5 cm.
(3) *Longevity of blooms on plant.*—24 days.
Sepal:
(1) *Number.*—About 20.

(2) *Color.*—Near 143A.
(3) *General Appearance.*—Acute tips, very tight, highly membraneous very little green on outer sepals; length about 0.6 cm, width about 0.3 cm; margin entire and membranous.

Peduncle:
(1) *Length.*—Average about 4.7 cm.
(2) *Habit.*—Upright with slight irregular curving.
(3) *Surface.*—Puberulent.
(4) *Color.*—Near 137D.
(5) *Strength.*—Slightly weak.

Bud:
(1) *Shape.*—Regular flattened sphere.
(2) *Diameter.*—Avg. about 0.7 cm.
(3) *Color.*—Near 146C.
(4) *Height.*—About 0.5 cm.

Ray florets:
(1) *Number per flower.*—Average about 24.
(2) *Fused.*—No.
(3) *Texture.*—Smooth, matte.
(4) *Shape.*—Tubular, changing ¾ to end.
(5) *Apex.*—3-lobed.
(6) *Base.*—Tubular at base, top ¾ of floret opens as a flat blade.
(7) *Margin.*—Entire.
(8) *Aspect.*—Flat.
(9) *Length.*—Average about 2.3 cm.
(10) *Width.*—Average about 0.5 cm at widest point.
*Color—top side.*—Immature: Near 8B. Mature: Near 10C. Fading: Near 11C.
*Color—under side.*—Immature: Near 8D with faint streaking of near 59B. Mature: Near 10C, with faint streaking of near 59B. Fading: Near 8C, with faint streaking of near 158D.

Disc florets:
(1) *Number per flower.*—Average about 152.
(2) *Texture.*—Smooth.
(3) *Shape*—Tubular.
(4) *Margin.*—Entire, 5-lobed.
(5) *Length.*—Average about 1.3 cm.
(6) *Width.*—Average about 0.2 cm.
(7) *Fragrance.*—Very faint, slightly sweet.
*Color.*—Immature: Near 4A, near 53A tip. Mature: Near 5C,near 46A tip. Fading: Near 5C, very little red, near 46A, still showing.

Description of flower as it ages: Ray floret shrivel and pink pigment becomes more obvious but not darker. Disc floret are farther apart making dark centers appear lighter.

Reproductive Organs

Ray floret:
*Pistillate.*—(1) Pistil number: 1 per floret. (2) Receptacle shape: Sphere, flattened on bottom. (3) Stigma shape: Forked, slight curve. (4) Stigma color: Near 9B. (5) Style length: About 0.4 cm. (6) Style color: Translucent white.

Disc floret: Both Staminate and Pistillate.
*Pistillate.*—(1) Pistil number: 1 per floret. (2) Stigma shape: Forked, slight curve, near 9B. (3) Style length: About 0.4 cm, translucent white.
*Staminate.*—(1) Stamen number: About 2. (2) Anther length: About 0.13 cm. (3) Anther shape: Oblong. (4) Pollen color: Near 12A. (5) Pollen quantity: Medium.

What is claimed is:

1. A new and distinct variety of Chrysanthemum plant as herein shown and described.

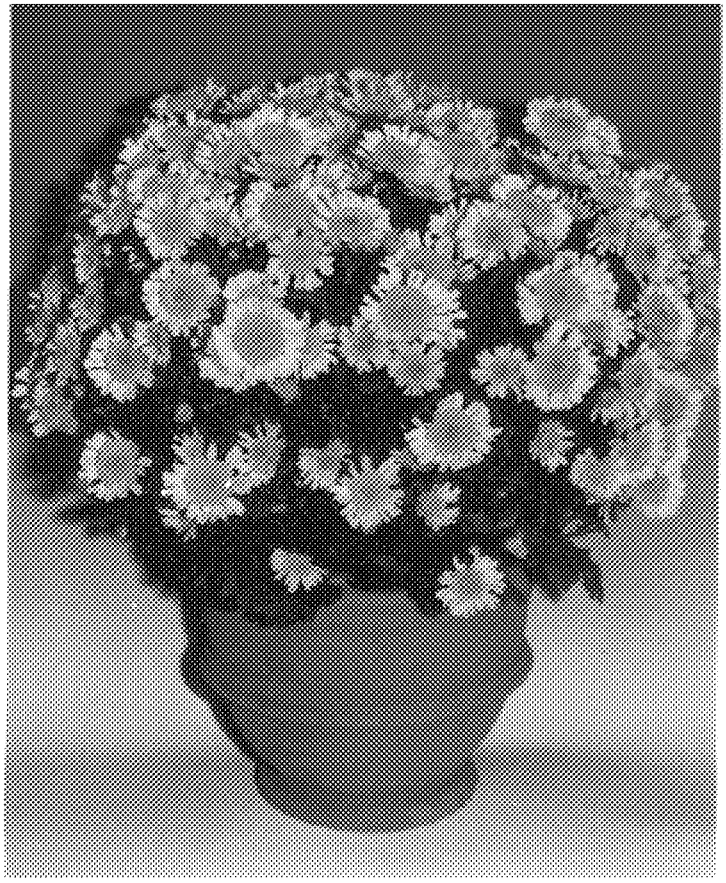

* * * * *